· US008675613B2

United States Patent
Ross et al.

(10) Patent No.: US 8,675,613 B2
(45) Date of Patent: Mar. 18, 2014

(54) APPARATUS AND METHOD OF OPTIMIZING SLOT LOCATIONS FOR WIRELESS SENSORS

(75) Inventors: John Anderson Fergus Ross, Niskayuna, NY (US); David Michael Davenport, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 893 days.

(21) Appl. No.: 12/016,489

(22) Filed: Jan. 18, 2008

(65) Prior Publication Data

US 2009/0185546 A1    Jul. 23, 2009

(51) Int. Cl.
*H04J 3/00*    (2006.01)

(52) U.S. Cl.
USPC ............ 370/336; 370/345; 370/442; 370/459

(58) Field of Classification Search
None
See application file for complete search history.

(56) References Cited

U.S. PATENT DOCUMENTS

| 2003/0114104 | A1 | 6/2003 | Want et al. | |
|---|---|---|---|---|
| 2003/0162556 | A1 | 8/2003 | Libes | |
| 2004/0013127 | A1* | 1/2004 | Shvodian | 370/442 |
| 2007/0206565 | A1* | 9/2007 | Evans | 370/352 |
| 2008/0058004 | A1* | 3/2008 | Gonorovsky et al. | 455/552.1 |
| 2009/0105567 | A1* | 4/2009 | Smith et al. | 600/323 |
| 2010/0128691 | A1* | 5/2010 | McFarland | 370/329 |

* cited by examiner

*Primary Examiner* — Faruk Hamza
*Assistant Examiner* — Tito Pham
(74) *Attorney, Agent, or Firm* — Scott J. Asmus (57) ABSTRACT

A wireless communication system includes a network controller configured to manage communication time periods in a wireless network, and a plurality of peripheral devices connected to the network controller through the wireless network. Each peripheral device is associated with a respective contiguous communication time period during which communications between the network controller and the peripheral device are allowed. The network controller is further configured to identify an open communication time period associated with one of the plurality of peripheral devices that has no communication between the network controller and the one of the plurality of peripheral devices and associate another of the plurality of peripheral devices that is associated with a different communication time period with the identified open communication time period.

18 Claims, 7 Drawing Sheets

APPARATUS AND METHOD OF OPTIMIZING SLOT LOCATIONS FOR WIRELESS SENSORS

BACKGROUND OF THE INVENTION

The invention relates generally to wireless sensor networks for patient monitoring and, more particularly, to communication between elements of a wireless patient sensor network.

Monitoring vital signs is an important part of patient care because the general or particular health of the patient is determined, in part, through measurement and interpretation of key physiological indicators. Well-known parameters of patient health include blood pressure, hemoglobin saturation, and features of the electrocardiogram (ECG).

However, the utilization of physiological instrumentation to obtain those measurements at bedside also presents well-known burdens in the clinical environment. The presence of cables, catheters, and tubes connecting the patient and sensors to the instrumentation can diminish productivity and the quality of patient care. For example, rotating a patient to alleviate bedsores or ambulating about the room can be problematic if one is saddled with tethered devices. Procedural delays stemming from cable management also contribute to a greater percentage of time dedicated to routine, mundane tasks not directly related to treatment of the patient's illness.

The longstanding burdens have remained unsolved for a variety of reasons. A major problem involves varying levels of care that one might receive in a hospital. A patient, for instance, may easily progress from low-acuity monitoring at admissions to high acuity monitoring within a specialized care unit, to a lower acuity level involving ordinary cardiac telemetry, and finally to discharge. To meet this need of evolving care, a variety of instrumentation has been developed to accommodate the monitoring needs. These monitoring instruments can be added or subtracted from the patient's monitoring regime, depending on the patient's needs. However, these adaptive needs only add to the burden of cable and device management.

Wireless communication technology leveraged to patient monitoring may at least circumvent some of the problems associated with cable clutter and device management. With instrumentation becoming wireless, management of such devices is eased. In addition, communication with wireless instrumentation/devices greatly reduces the burdens associated with cable management.

Wireless patient monitoring networks, however, bring new problems that are also common to other wireless communication systems. Whether using a wireless patient monitoring network or another wireless communication system, the need to reduce cable clutter often requires that many elements of the network or system be battery powered. This, in turn, brings energy constraints that are not typically seen in wired systems. These constraints increase the need for energy efficient wireless elements and the networks or systems they are a part of.

In addition, not only is there a need for the wireless network or system to function in an energy efficient manner, there is also a need for the system or network to function in a spectrally efficient manner. As the number of wireless communication systems, networks, and/or elements of such systems and networks increases, media access may be limited as operation of one system may interfere with that of another. As such, there is also a need to manage, in a spectrally efficient manner, the operation of multiple systems or networks.

Therefore, it would be desirable to design an apparatus and method that minimizes not only the media access time and energy demand of wireless devices used in wireless systems, but also minimizes the media access time and energy demand of one or more entire wireless systems.

BRIEF DESCRIPTION OF THE INVENTION

The invention provides a system and method for communication between elements of a wireless network that overcomes the aforementioned problems. A management device organizes the temporal placement of sensor communication times such that multiple sensors communicate in time slots that are contiguous with each other, thereby optimizing media access time and improving the energy efficiency thereof.

In accordance with one aspect of the invention, a wireless communication system includes a network controller configured to manage communication time periods in a wireless network and a plurality of peripheral devices connected to the network controller through the wireless network, each peripheral device associated with a respective contiguous communication time period during which communications between the network controller and the peripheral device are allowed. The network controller is further configured to identify an open communication time period associated with one of the plurality of peripheral devices that has no communication between the network controller and the one of the plurality of peripheral devices and associate another of the plurality of peripheral devices that is associated with a different communication time period with the identified open communication time period.

According to another aspect of the invention, a method for managing a wireless communication system includes assigning each of a plurality of peripheral devices to a respective one of a plurality of communication time periods of a wireless network, identifying, from the plurality of communication time periods, a first communication time period occurring between a pair of communication time periods, wherein the first communication time period has no communication between the peripheral device assigned thereto and a network controller, and re-assigning the peripheral device that is assigned to one of the pair of communication time periods to the first communication time period.

According to yet another aspect of the invention, a computer readable storage medium having stored thereon a computer program comprising instructions which when executed by a computing device cause the computing device to instruct each of a plurality of wireless sensor devices to transmit sensor information to the computing device during a respective contiguous time frame such that each contiguous time frame corresponds to a respective wireless sensor device, identify an open time frame corresponding to a first wireless sensing device of the plurality of wireless sensor devices that is void of sensor information transmission to the computing device, and instruct a second wireless sensing device of the plurality of wireless sensing devices to transmit sensor information to the computing device during the identified open time frame.

Various other features and advantages of the invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
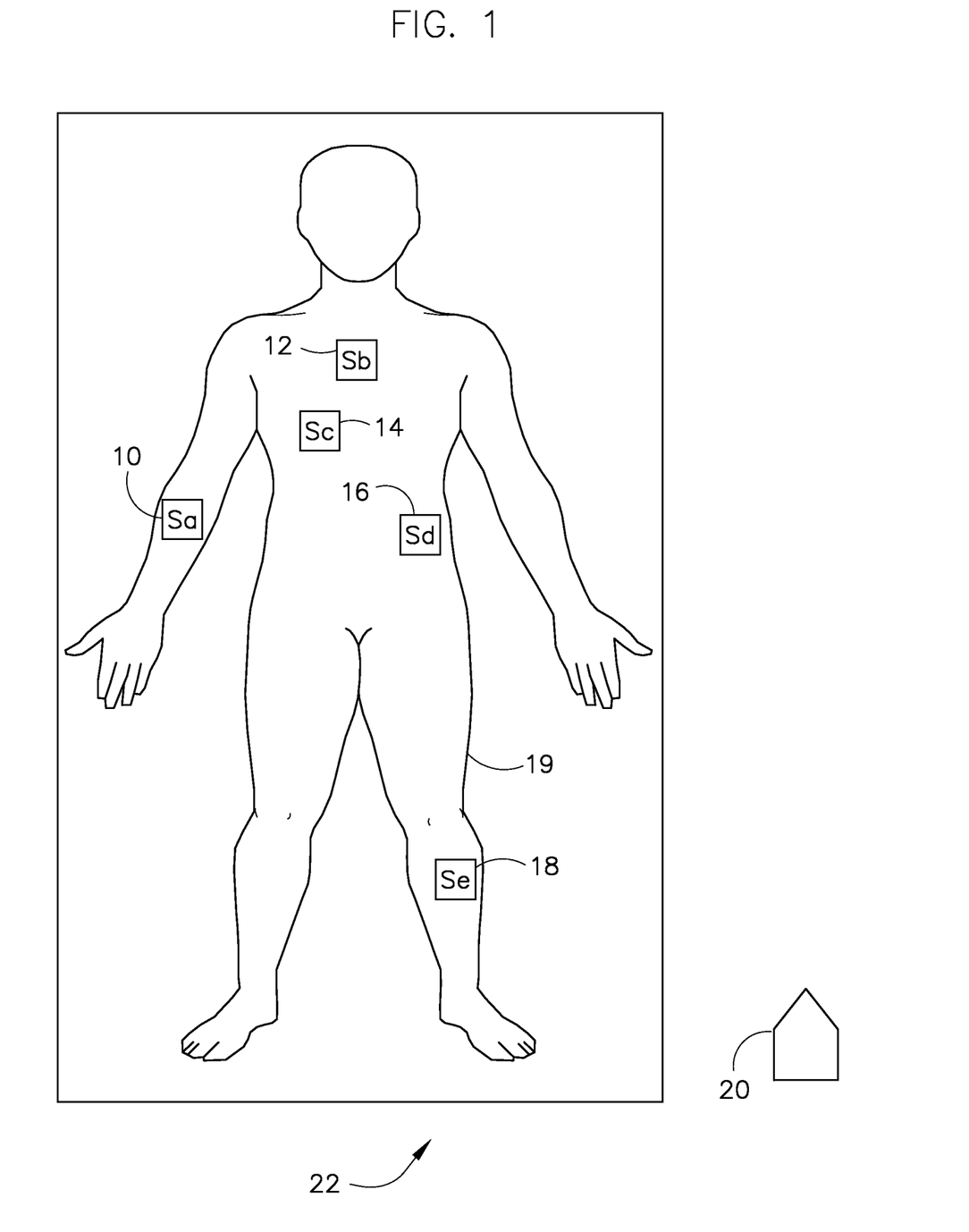
FIG. 1 is a pictorial illustration depicting one embodiment of a wireless network associated with a patient.

Referring to FIG. 1, an embodiment of the invention is shown in a pictorial depiction of a wireless network 22 having wireless sensors $S_a$-$S_e$ (10-18) attached to a patient 19. Multiple peripheral devices, or sensors 10-18 are shown, and each communicates wirelessly with a network controller or management device 20. As will be described more fully with respect to FIGS. 2-6, management device 20 governs media access time of sensors 10-18 by instructing sensors 10-18 when to communicate sensor information and when to receive management information. The management device 20 may, like the wireless sensors $S_a$-$S_e$ (10-18), be a body worn device. In the alternative, the management device 20 may reside at the patient's 19 bedside or other location. The instructions from management device 20 minimize energy demands ensure efficient use of the operating time of network 22, and ensure deterministic access to the wireless link by sensors 10-18. Though the embodiment shows five wireless sensors 10-18, it is contemplated that wireless network 22 could contain more than or less than the five sensors 10-18 shown.

Figure 2:
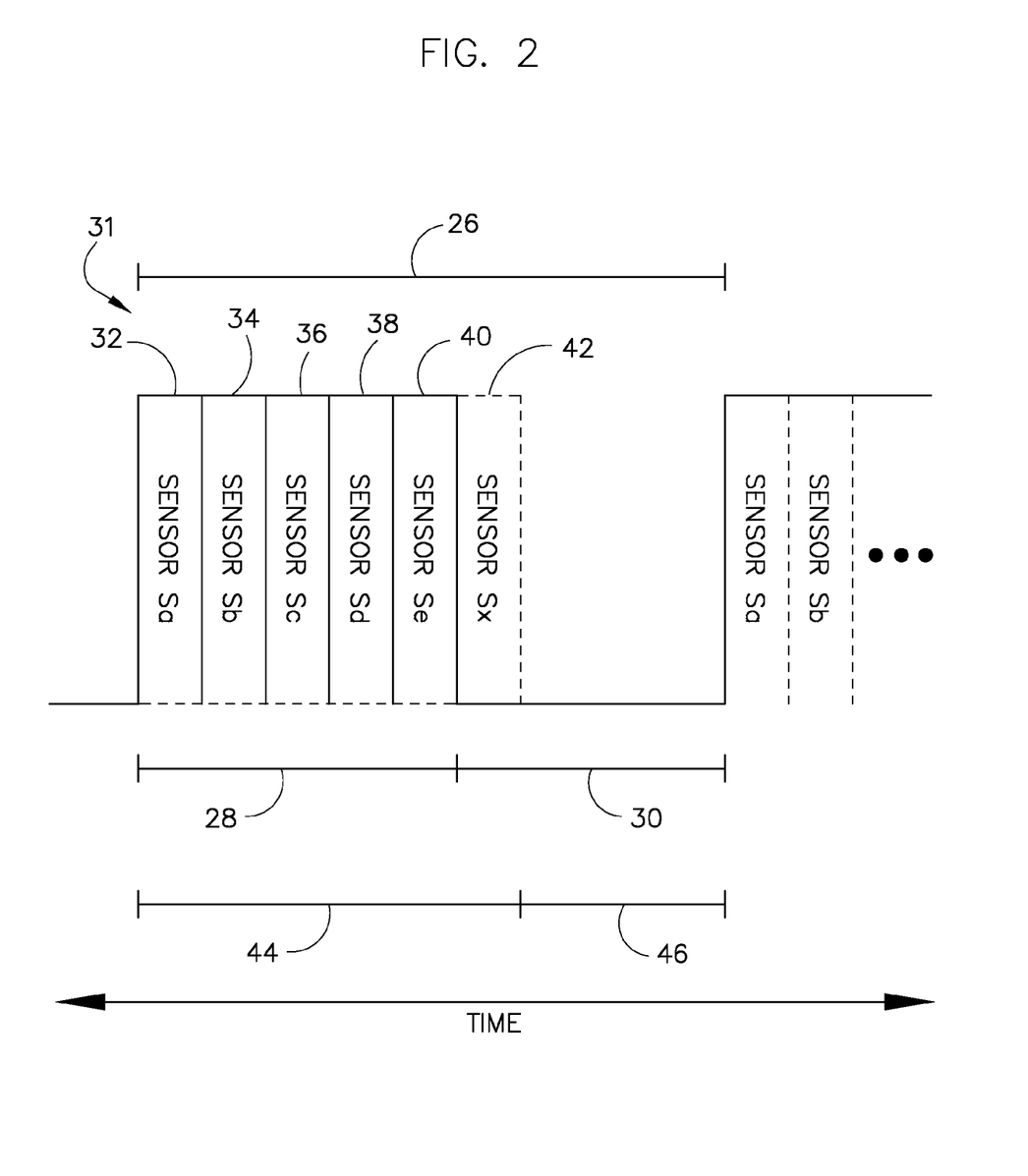
FIG. 2 illustrates one embodiment of a duty cycle of the wireless network of FIG. 1.

Referring to FIG. 2, a duty cycle 26 of network 22 shown in FIG. 1 is illustrated according to an embodiment of the invention. Duty cycle 26 generally consists of an active time frame 28 and an inactive or sleep time frame 30. Active time frame 28 is dynamic, and, during this frame, sensors $S_a$-$S_e$ communicate bi-laterally with management device 20 of FIG. 1. Sleep time frame 30 is also dynamic, and, during sleep time frame 30, sensors $S_a$-$S_e$ and the management device 20 are able to go into sleep mode to at least minimize energy demand and make efficient use of the operating time of network 22. A communication period group 31 includes communication time periods or time slots 32-40 that are the time intervals when respective sensors $S_a$-$S_e$ communicate with management device 20 of FIG. 1. These time slots 32-40 are associated with the respective sensors $S_a$-$S_e$ through instructions from management device 20.

Additional sensors may be added to the network, which may require dynamic adjustment of the network operation and of communication period group 31. As an example, an additional time slot 42, illustrated in phantom, represents a time period that would be associated, by management device 20, with a new sensor $S_x$, which may be placed on patient 19 of FIG. 1. As illustrated in FIG. 2, if sensor $S_x$ is brought into the network 22, active time frame 28 will dynamically change to a longer active time frame 44. Conversely, sleep period 30 likewise dynamically changes to a shorter sleep period 46. Per the instruction of management device 20, communication period group 31 and sensors $S_a$-$S_x$ are managed such that sensors $S_a$-$S_x$ communicate with management device 20 during respective time slots 32-42 that are contiguous with each other. When not communicating during its time slot, each sensor $S_a$, $S_e$, $S_c$, $S_d$, and $S_x$ may enter a sleep mode during the other time slots to conserve energy. Accordingly, communications transmitted during contiguous time slots 32-42 minimizes energy demand and also makes efficient use of the duty cycle 26 of network 22. With regard to minimizing energy demand, by ensuring that the time slots 32-40 are contiguous with one another, the management device's 20 wireless receiver (not shown) of management device 20 will not need to remain on for the entire duty cycle 26. Further, the cumulative warm-up and shut-down time of the management device receiver is reduced compared to a situation in which the time slots 32-40 were not contiguous. In other words, the management device receiver will not need to remain on for the entire duty cycle 26 and will only need to warm-up and shut-down once for each duty cycle 26.

One skilled in the art will recognize that, although the duty cycle of FIG. 2 begins at the start of the active period 28 and ends after the sleep period 30, it is contemplated that a duty cycle may be defined to begin and end at any cyclical interval within duty cycle 26. One skilled in the art will also recognize that communication time slots 32-42, although illustrated as having substantially equal durations of time, may have differing durations of time such that the resulting active time frame 28 represents the sum of the time slots 32-42 when the communication periods 32-42 are contiguously operated.

Figure 3:
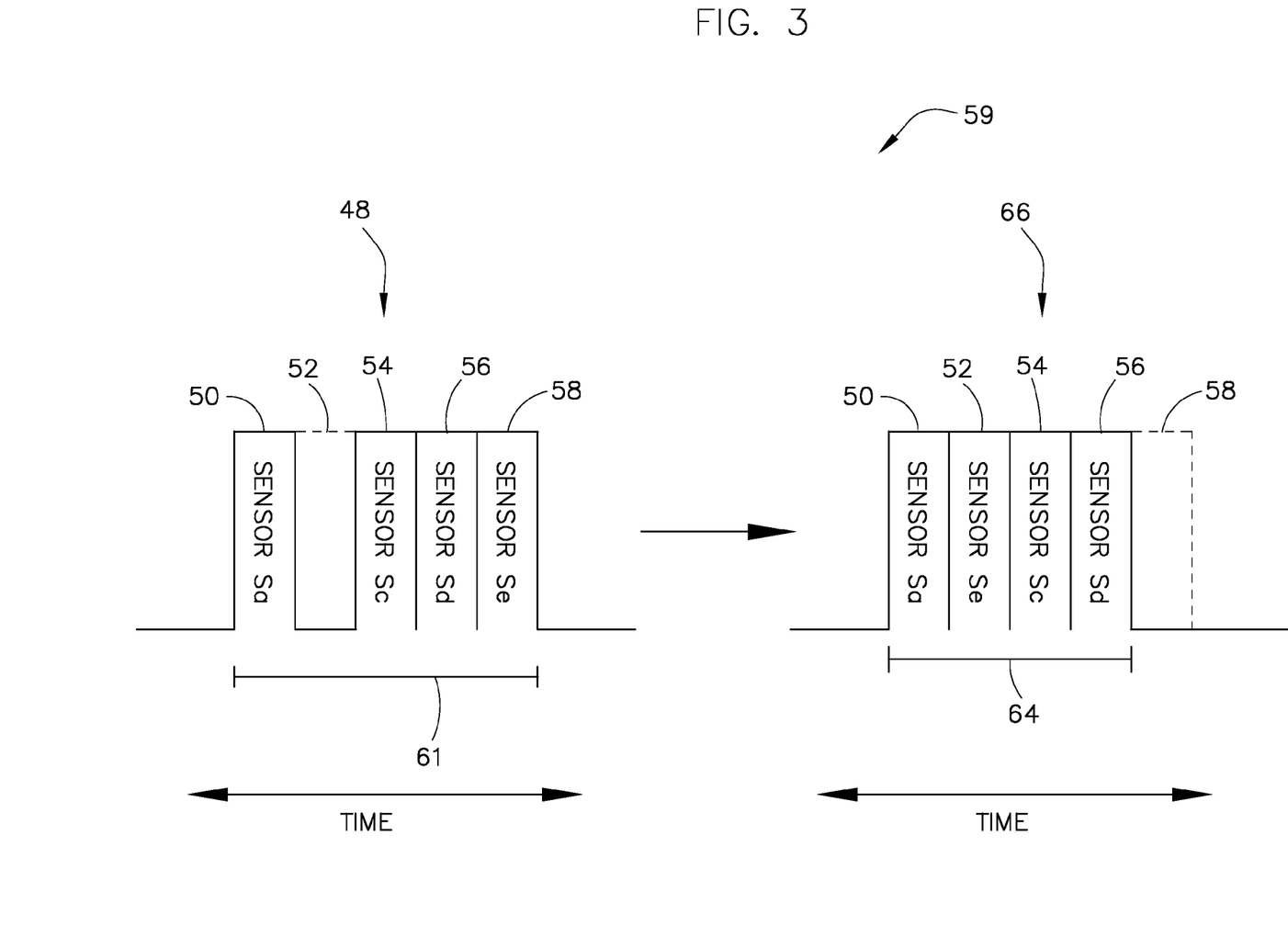
FIG. 3 illustrates one embodiment of a management scheme of the wireless network shown in FIG. 1.

Referring now to FIG. 3, a management scheme 59 for modifying communication time periods when communications during one of the communication time periods fail is illustrated according to an embodiment of the invention. A communication period group 48 during an active period 61 includes continuous time slots 50-58 to which sensors $S_a$-$S_e$ have been assigned. However, as illustrated in communication period group 48, communications from sensor $S_b$ are no longer received. In an example, sensor $S_b$ has failed or is no longer in the network 22, leaving an unused time slot 52. As such, management device 20 determines that time slot 52 is unused. In the embodiment shown in FIG. 3, management device 20 instructs and re-assigns sensor $S_e$ to transmit during the empty slot 52 and to no longer transmit at its present time slot 58. In another embodiment, when communication has ceased and no communication is detected with, for instance, a sensor associated with time slot 52, the management device 20 may execute a one-way disassociation procedure to remove the sensor assigned thereto, and re-assign a sensor to the empty time slot according to the embodiments described herein.

Thus, still referring to FIG. 3, represented in communication period group 66 is a modified active period 64, wherein the time slot for sensor $S_e$ is shifted to time slot 52 from its previous time slot 58 as shown in communication period group 48. Thus, sensors $S_a$, $S_e$, $S_c$ and $S_d$ communicate during time slots 50, 52, 54, 56, respectively, and are contiguous in the active period 64. In this embodiment, the transition of sensor $S_e$ between time slots 58 and 52 occurs within one duty cycle 26 (shown in FIG. 2). That is, after detecting that time slot 52 is open, the next communication with sensor $S_e$ results in its re-assignment from time slot 58 to time slot 52. It is contemplated, however, that the management device 20 may allow one or more duty cycles 26 to pass before instructing the transition of sensor $S_e$ to its new contiguous time slot 52.

As such, where the active period 61 included five time slots 50-58, when communications between management device 20 and sensor $S_b$ fails, communications with sensor $S_e$ is thus shifted from time slot 58 to time slot 52, thus resulting in a reduced active period 64, as illustrated in the second signal packet 66. Accordingly, energy demand is reduced and the overall transmission efficiency is improved.

Figure 4:
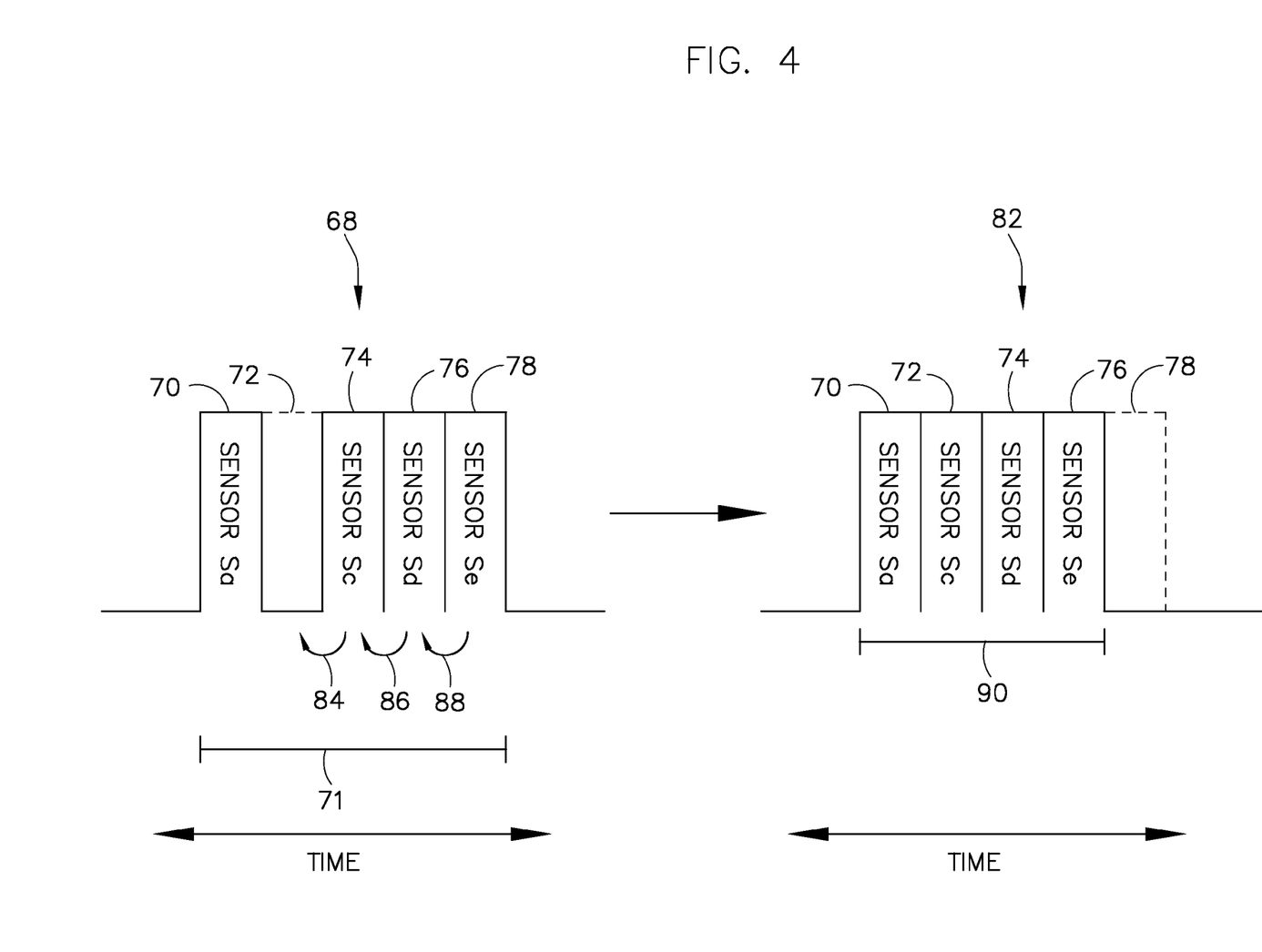
FIG. 4 illustrates another embodiment of a management scheme of the wireless network shown in FIG. 1.

Referring now to FIG. 4, an alternate scheme for managing sensors $S_a$, $S_c$, $S_d$ and $S_e$ is shown according to another embodiment of the invention. Communication period group 68 shows an active period 71 including time slot 72 for which communications with sensor $S_b$ has failed. In the embodiment shown in FIG. 4, management device 20 serially instructs the sensors corresponding to time slots. Accordingly, management device 20 instructs sensor $S_c$ to transition 84 communications to the empty slot 72. Likewise, communications with sensor $S_d$ transitions 86 to time slot 74, and communications with sensor $S_e$ transitions 88 to time slot 76. As such, communication period group 82 represents the modified set of sensor transmissions for sensors $S_a$, $S_c$, $S_d$, and $S_e$, having only four time slots 70-76. Accordingly, because communications with sensor $S_b$ have failed, the subsequent sensor transmissions $S_c$, $S_d$, and $S_e$ have been consolidated into a transmission time packet 90. The later time slot 78 is unused, and the active slots 70, 72, 74, and 76 are contiguously transmitted in a time packet 90 that is shorter than the original time packet, or active period 71.

The embodiments shown in FIGS. 3 and 4 represent two schemes for managing sensors $S_a$, $S_b$, $S_c$, $S_d$ and $S_e$. It is contemplated, however, that any variation of sensor re-arrangement can occur. As an example, one skilled in the art will recognize that, for instance, communications with two sensors may fail, thus a communication period group may be further consolidated into a group having only three contiguous transmission segments therein. One skilled in the art will further recognize that, in a situation where consolidation of two has occurred, the two segments may or may not have been contiguous prior to consolidation.

Figure 5:
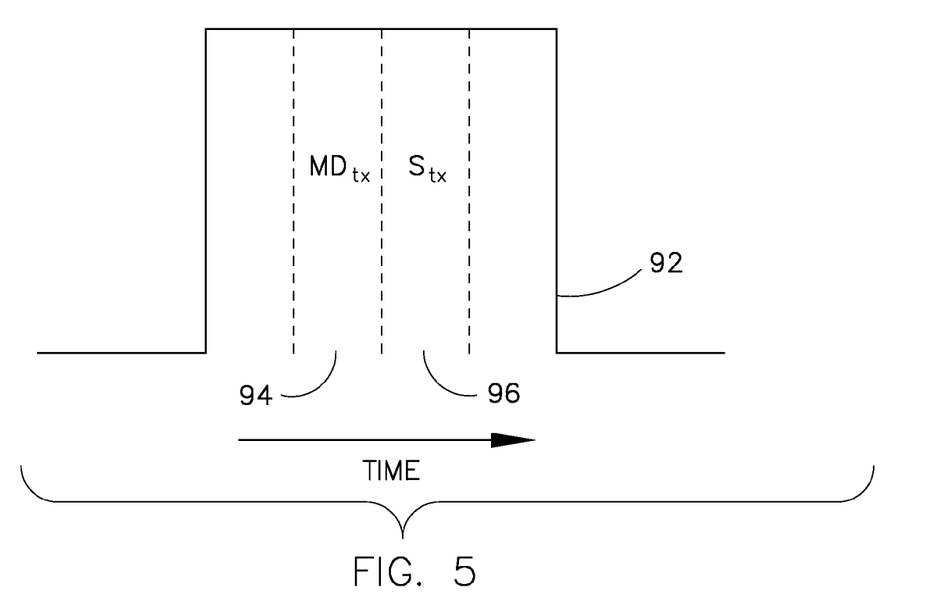
FIG. 5 illustrates one embodiment of the temporal order of sensor and management device communication within one time slot.

The time slots described above may each comprise transmission from both sensors and management device. Referring now to FIG. 5, an embodiment illustrating both management device transmission ($MD_{tx}$) and sensor transmission ($S_{tx}$) within a single time slot 92 is shown. In this embodiment, the time slot 92 is a time frame in which a single sensor, such as one of the sensors 10-18 shown in FIG. 1, communicates with the management device 20. In this embodiment, management device transmission ($MD_{tx}$) 94 occurs before sensor transmission ($S_{tx}$) 96.

During the management device transmission time period 94, management device 20 transmits information such as an instruction when to transmit information in a future time slot. Likewise, during the sensor transmission time period 96, the sensor transmits information from the sensor to the management device 20. By having the management device transmit 94 before the sensor transmission 96, synchronization drift may be minimized. However, one skilled in the art will recognize that the order of transmission time periods 94, 96 may be reversed.

Figure 6:
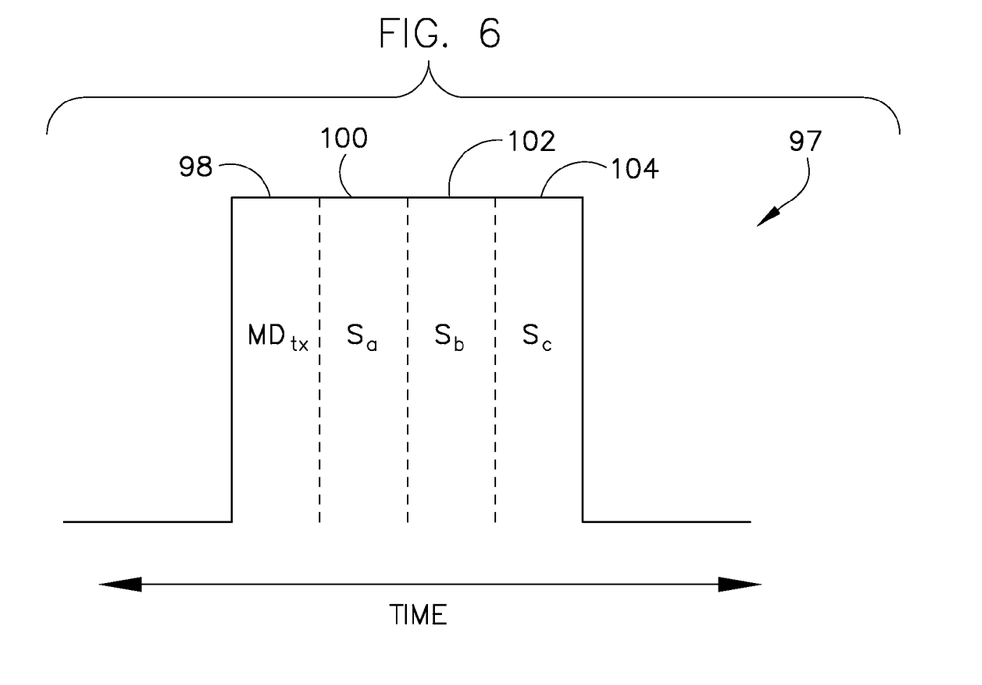
FIG. 6 illustrates one embodiment of the temporal order of sensor and management device transmission communication within a group.

FIG. 6 illustrates an embodiment of the invention where the management device transmission ($MD_{tx}$) and sensor transmission ($S_{tx}$) occur in separate time slots. During time slot 98, sensors $S_a$-$S_c$ may receive an instruction or an assignment from the management device via management device transmission ($MD_{tx}$) that provides instructions on when individual transmissions should occur. For example, sensors $S_a$-$S_c$ may be instructed during time slot 98 to transmit during time slots 100-104, respectively. In this instance, sensors $S_a$-$S_c$ would awake during time slot 98 to receive transmission instruction from the management device and then sleep until they transmit during their assigned slot 100-104, respectively. Though FIG. 6 depicts the management device transmission ($MD_{tx}$) occurring during the first time slot 98 of the group 97, it is contemplated that the management device transmission ($MD_{tx}$) may be rearranged such that the management device transmission ($MD_{tx}$) instruction occurs after or between time slots 100-104 of group 97.

Figure 7:
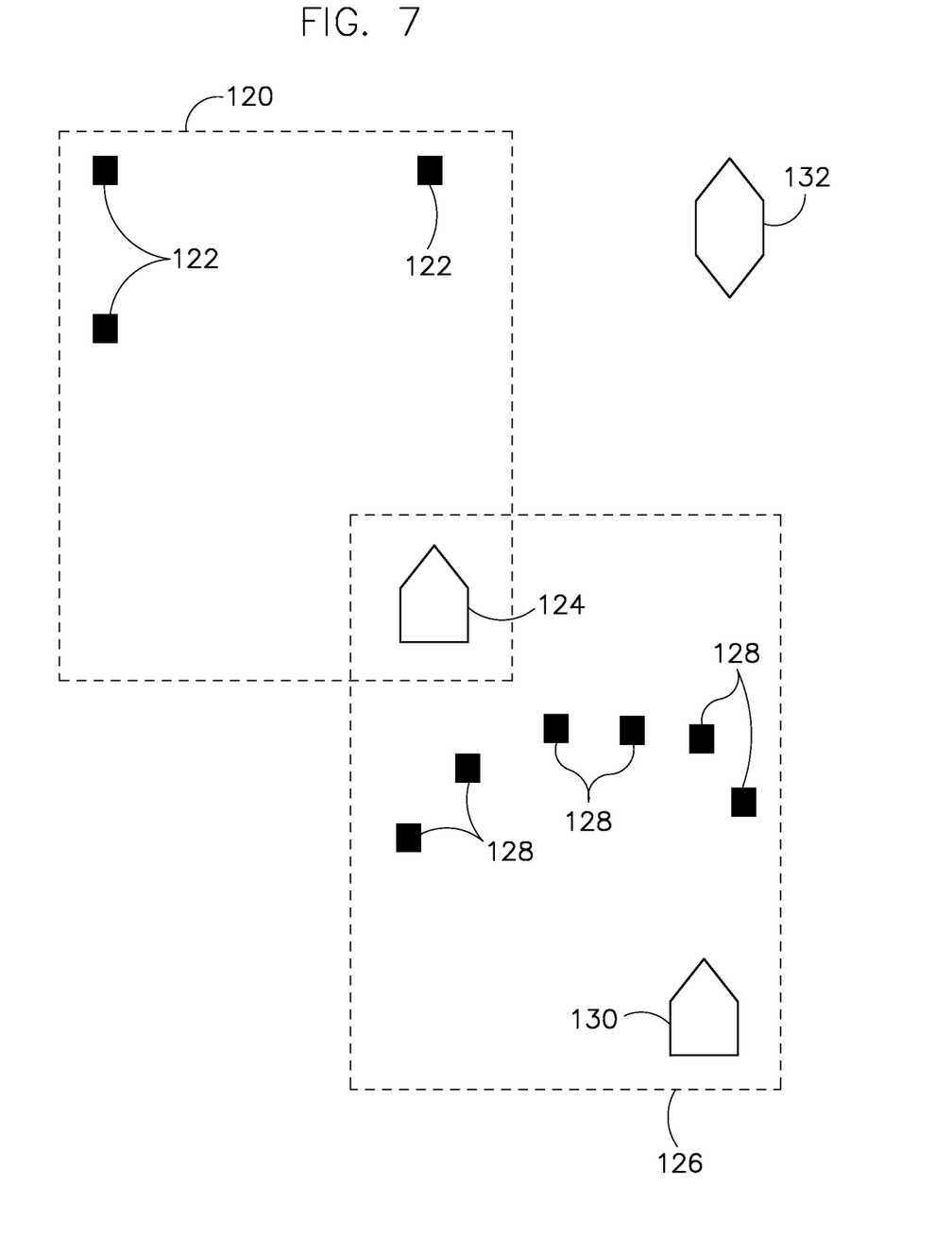
FIG. 7 is a pictorial illustration depicting one embodiment of two wireless networks having a common management device and functioning within the vicinity of one another.

Referring now to FIG. 7, two networks 120, 126 having a super-management device 132 are illustrated according to an embodiment of the invention. In this embodiment, a first network 120 consists of a grouping of three sensors 122 and a management device 124. A second network 126 consists of six sensors 128 and a management device 130. The super-management device 132 manages, as will be set forth with respect to FIG. 8, the two management devices 124, 130. It is contemplated, however, that the super-management device 132 may be configured to manage more than or less than the two management devices, 124 130, as shown. Furthermore, it is contemplated that the networks 120, 126 may contain more or less sensors 122, 128 than those shown.

The super-management device 132 manages the media access time of the networks 120, 126, such that interference therebetween is minimized, power requirements are minimized, and media access time is efficiently used. Device 132 accomplishes the management duties by gathering and efficiently using temporal information from the management devices, 124, 130. The information may include, but is not limited to, active time frames 28, sleep time frames 30, and duty cycles 26 as illustrated in FIG. 2. As will be described more fully with respect to FIG. 8, using temporal information about the networks 120, 126, the super-management device 132 instructs the management devices 124, 130 when their networks 120, 126 should be active.

Figure 8:
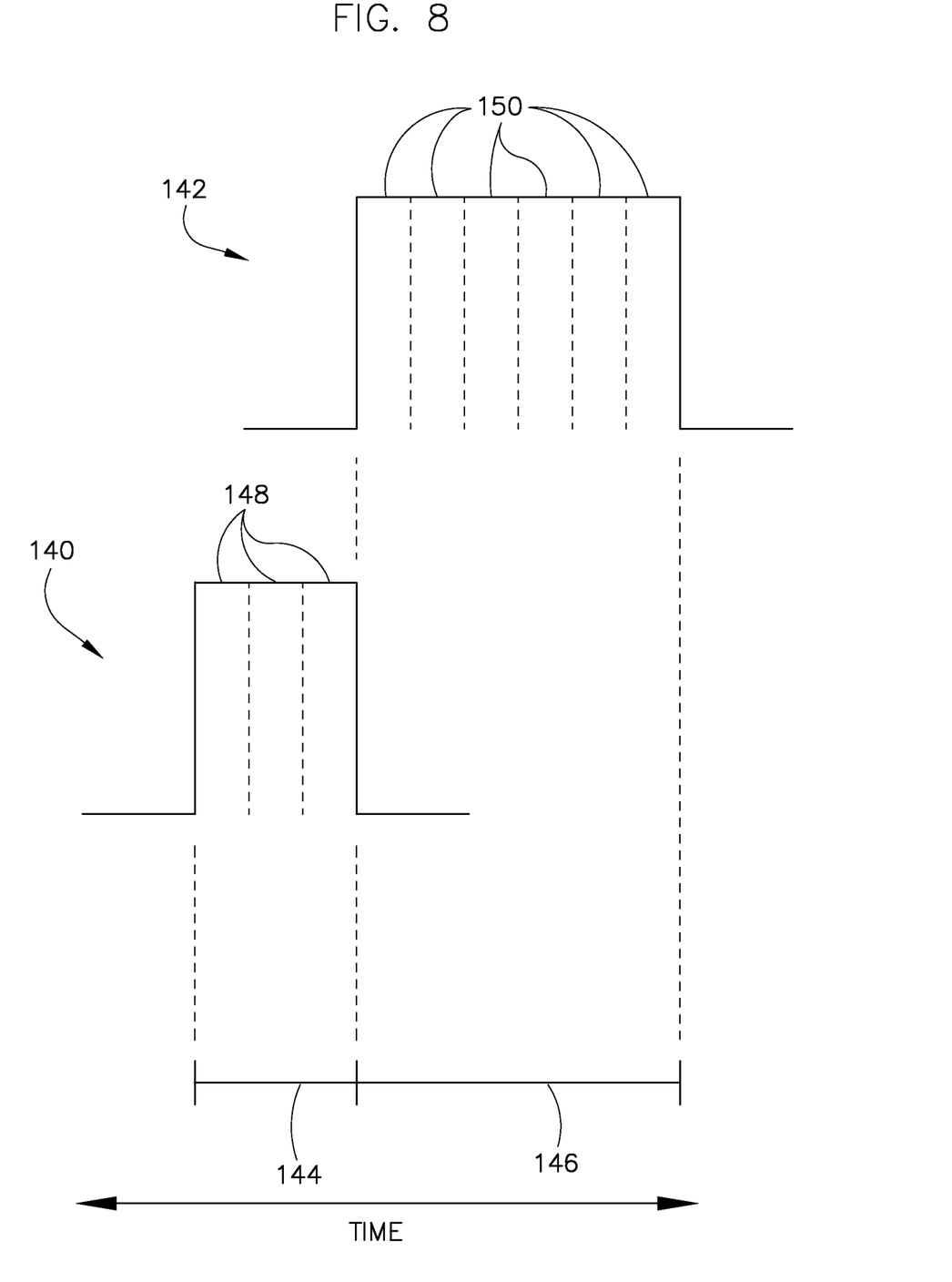
FIG. 8 is a pictorial representation depicting management of the active periods of the two networks shown in FIG. 7.

Referring now to FIGS. 8 and 7, an embodiment of the invention is illustrated in which the super-management device 132 may manage two active time frames 140, 142, each having, respectively, time slots 148 and 150. That is, the super-management device 132 may assign a temporal placement 144, 146 of a time frame 140, 142, which is comprised of a plurality of communication time periods 148, 150, respectively. In this embodiment, as an example, the two active time frames 140, 142 represent data that corresponds to the two networks 120, 126, respectively. The super-management device 132 is configured to receive consolidated data from both active frames 140, 142. In other words, data in both time frames 140, 142 represents sensor data that may be consolidated according to embodiments of the invention described above. Once the data in both time frames 140, 142 is identified, the super-management device 132 then determines the temporal placement of the active frames 140, 142, made up of contiguous communication time slots 148 and 150, in such a manner that the active frames 140, 142 of, for instance, management devices 124, 130 do not overlap in time 144, 146, thus making efficient use of media access time with data from both networks 120, 126 without causing interference therebetween.

Though FIG. 8 shows the active periods 144, 146 temporally adjacent to one another, it is contemplated that the active periods 144, 146 need not be contiguous. That is, it is contemplated that the active periods 144, 146 may be separated by a time interval determined appropriate by the super-management device 132. In addition, it is also contemplated that less than or more than two networks may be managed by the super-management device 132, while still ensuring that the respective active periods do not temporally overlap, thus minimizing overall power usage and improving overall system transmission efficiency.

A technical contribution for the disclosed method and apparatus is that it provides for a computer implemented wireless sensor network for patient monitoring and communication between elements of a wireless patient sensor network.

Therefore, according to one embodiment of the invention, a wireless communication system includes a network controller configured to manage communication time periods in a wireless network and a plurality of peripheral devices connected to the network controller through the wireless network, each peripheral device associated with a respective contiguous communication time period during which communications between the network controller and the peripheral device are allowed. The network controller is further configured to identify an open communication time period associated with one of the plurality of peripheral devices that has no communication between the network controller and the one of the plurality of peripheral devices and associate another of the plurality of peripheral devices that is associated with a different communication time period with the identified open communication time period.

According to another embodiment of the invention, a method for managing a wireless communication system includes assigning each of a plurality of peripheral devices to a respective one of a plurality of communication time periods of a wireless network, identifying, from the plurality of communication time periods, a first communication time period occurring between a pair of communication time periods, wherein the first communication time period has no communication between the peripheral device assigned thereto and a network controller, and re-assigning the peripheral device that is assigned to one of the pair of communication time periods to the first communication time period.

According to yet another embodiment of the invention, a computer readable storage medium having stored thereon a computer program comprising instructions which when executed by a computing device cause the computing device to instruct each of a plurality of wireless sensor devices to transmit sensor information to the computing device during a respective contiguous time frame such that each contiguous time frame corresponds to a respective wireless sensor device, identify an open time frame corresponding to a first wireless sensing device of the plurality of wireless sensor devices that is void of sensor information transmission to the computing device, and instruct a second wireless sensing device of the plurality of wireless sensing devices to transmit sensor information to the computing device during the identified open time frame.

The invention has been described in terms of the preferred embodiment, and it is recognized that equivalents, alternatives, and modifications, aside from those expressly stated, are possible and within the scope of the appending claims.

What is claimed is:

1. A wireless patient monitoring system comprising:
two or more network controller devices managing communication time periods in a wireless patient sensor network;
a plurality of peripheral devices comprising one or more patient monitoring sensors connected to a network controller device in the two or more network controller devices through the wireless patient sensor network, each peripheral device associated with a respective contiguous communication time period within an active time period during which communications between the network controller device and the peripheral device are allowed;
wherein the network controller device:
identifies an open communication time period associated with one of the plurality of peripheral devices, wherein the plurality of the peripheral devices have no communication with the network controller device; and
associates the open communication time period to another of the plurality of peripheral devices in place of a different communication time period that was previously associated with said another of the plurality of peripheral devices such that the active time period is reduced and the plurality of peripheral devices is configured to communicate in contiguous communication time periods within the reduced active time period,
a super-management device controlling the two or more network controller devices, wherein the two or more network controller devices are controlled by the super-management device such that active communication time periods of each of the two or more network controllers are contiguous, such that active communication time periods of one of the two or more network controllers are contiguous with the active communication time periods of another of the two or more network controllers, or a combination thereof, such that interference therebetween is minimized.

2. The wireless communication system of claim 1 wherein the network controller device associates each of the plurality of peripheral devices with the contiguous communication time period.

3. The wireless communication system of claim 1 one or more of the plurality of peripheral devices and the network controller device is a battery-operated device.

4. The wireless communication system of claim 1 wherein the network controller device disassociates from and ceases further communication with the one of the plurality of peripheral devices that has no communication with the network controller device.

5. The wireless communication system of claim 1 wherein each of the plurality of peripheral devices connected to the network controller device communicates sensor information during its associated communication time period.

6. The wireless communication system of claim 1 wherein each communication time period includes a peripheral device transmission period and a management device transmission period, wherein the network controller device transmits information during the management device transmission period.

7. The wireless communication system of claim 6 wherein the management device transmission period occurs before the peripheral device transmission period.

8. A method for managing a wireless patient monitoring system comprising the steps of:
controlling two or more network controller devices that manage communication time periods in a wireless patient sensor network through a super-management device, wherein the two or more network controller devices are controlled by the super-management device such that active communication time periods of each of the two or more network controllers are contiguous, such that active communication time periods of one of the two or more network controllers are contiguous with the active communication time periods of another of the two or more network controllers, or a combination thereof, such that interference therebetween is minimized;
assigning each of a plurality of peripheral devices comprising one or more patient monitoring sensors to a respective one of a plurality of communication time periods within an active period of the wireless patient sensor network, wherein the plurality of peripheral devices is connected to a network controller device in the two or more network controller devices;

identifying, from the plurality of communication time periods, a first open communication time period occurring between a pair of communication time periods and assigned to a peripheral device in the plurality of peripheral devices, wherein the peripheral device has no communication with a network controller device during the first open communication time period; and re-assigning the first open communication time period to one of the peripheral devices in place of the pair of communication time periods that was previously assigned to the peripheral device such that the active time period is reduced and the plurality of peripheral devices is configured to communicate in contiguous communication time periods within the reduced active time period.

9. The method of claim 8 wherein each of the plurality of communication time periods includes a peripheral device transmission period and a management device transmission period, wherein the network controller device transmits information during the management device transmission period.

10. The method of claim 8 wherein the communication time periods in the plurality of communication time periods are contiguous.

11. The method of claim 8 further comprising a step of assigning a temporal placement of a first time frame comprising the plurality of communication time periods such that the first time frame does not overlap in time with a second time frame comprising another plurality of communication time periods.

12. A non-transitory computer readable storage medium having stored thereon a computer program comprising instructions which when executed by a computing device cause the computing device to:

control two or more network controller devices that manage communication time periods in a wireless patient sensor network through a super-management device, wherein the two or more network controller devices are controlled by the super-management device such that active communication time periods of each of the two or more network controllers are contiguous, such that active communication time periods of one of the two or more network controllers are contiguous with the active communication time periods of another of the two or more network controllers, or a combination thereof, such that interference therebetween is minimized, wherein the computing device comprises the super-management device;

instruct each of a plurality of wireless sensor devices comprising one or more portable patient monitors to transmit sensor information to the computing device during a respective contiguous time frame within an active period such that each contiguous time frame corresponds to a respective wireless sensor device, wherein the plurality of wireless sensor devices is connected to a first network controller device in the two or more network controller devices;

identify an open unused time frame corresponding to a first wireless sensing device of the plurality of wireless sensor devices that is void of sensor information transmission to the computing device; and instruct a second wireless sensing device of the plurality of wireless sensor-devices to transmit sensor information to the computing device during the identified open unused time frame in place of a different time frame that was previously assigned to the second wireless sensing device such that the active time period is reduced and the plurality of wireless sensor devices is configured to communicate in contiguous time frames within the reduced active time period.

13. The non-transitory computer readable storage medium of claim 12 wherein the computing device is further caused to:

control transmission of the plurality of wireless sensor devices using the first network controller device; and cause a second network controller device in the two or more network controller devices to transmit sensor information based on input from the first network controller device, such that transmissions from the first network controller device and the second network controller device do not interfere with one another.

14. The non-transitory computer readable storage medium of claim 13 having further instructions to cause the computer to create a computing device transmission period for the computing device, a network controller transmission period for the first network controller device, or a combination thereof.

15. The non-transitory computer readable storage medium of claim 14 having further instructions to cause the controller transmission period to occur before a wireless patient sensor device transmission period.

16. The non-transitory computer readable storage medium of claim 14 wherein both the controller transmission period and the sensor device transmission period are contiguous with each other.

17. The non-transitory computer readable storage medium of claim 12 wherein the computing device is further caused to disassociate itself from and cease further communication with the first wireless sensing device.

18. The non-transitory computer readable storage medium of claim 12 wherein at least one of the plurality of wireless sensor devices is a patient monitoring sensor.

* * * * *